(12) United States Patent
Lovchik et al.

(10) Patent No.: US 11,766,393 B2
(45) Date of Patent: Sep. 26, 2023

(54) SKIN CARE COMPOSITION COMPRISING ACETYLATED HYALURONIC ACID WITH DEGREE OF ACETYLATION QUANTIFIED BY 2D-MR

(71) Applicant: GIVAUDAN SA, Vernier (CH)

(72) Inventors: Martin Lovchik, Duebendorf (CH); Gerhard Brunner, Opfikon (CH); Romain Reynaud, Reims (FR); Amandine Scandolera, Reims (FR)

(73) Assignee: GIVAUDAN SA, Vernier (CH)

( * ) Notice: Subject to any disclaimer, the term of this patent is extended or adjusted under 35 U.S.C. 154(b) by 0 days.

(21) Appl. No.: 17/399,588

(22) Filed: Aug. 11, 2021

(65) Prior Publication Data
US 2021/0369592 A1    Dec. 2, 2021

Related U.S. Application Data

(63) Continuation of application No. 16/486,710, filed as application No. PCT/EP2018/055823 on Mar. 8, 2018, now abandoned.

(30) Foreign Application Priority Data

Mar. 10, 2017   (GB) ..................... 1703850

(51) Int. Cl.
| | |
|---|---|
| A61K 8/73 | (2006.01) |
| A61Q 19/08 | (2006.01) |
| C08B 37/08 | (2006.01) |

(52) U.S. Cl.
CPC .............. *A61K 8/735* (2013.01); *A61Q 19/08* (2013.01); *C08B 37/0072* (2013.01); *A61K 2800/782* (2013.01)

(58) Field of Classification Search
None
See application file for complete search history.

(56) References Cited

U.S. PATENT DOCUMENTS

| | | | | |
|---|---|---|---|---|
| 6,489,467 B1 * | 12/2002 | Carlino | ................ | C12P 19/26 536/53 |
| 2006/0166930 A1 * | 7/2006 | Ueno | ................ | C08B 37/0072 514/54 |
| 2009/0068255 A1 * | 3/2009 | Yu | ................ | A61Q 19/005 424/450 |
| 2015/0152459 A1 * | 6/2015 | Pagliuca | ................ | C12R 1/46 435/84 |

FOREIGN PATENT DOCUMENTS

| | | |
|---|---|---|
| CN | 106109296 A | 11/2016 |
| CN | 106176286 A | 12/2016 |
| EP | 0725083 A1 | 8/1996 |
| EP | 1598371 A1 | 11/2005 |
| EP | 2444058 A1 | 4/2012 |
| EP | 2644188 A1 | 10/2013 |
| JP | H069707 A | 1/1994 |
| JP | H0853501 A | 2/1996 |
| JP | H10279418 A | 10/1998 |
| JP | H10279419 A | 10/1998 |
| JP | H 10279425 A * | 10/1998 ............... A61K 8/00 |
| JP | H10279426 A | 10/1998 |
| JP | 2005068073 A | 3/2005 |
| JP | 2008280430 A | 11/2008 |
| KR | 20150015209 A | 2/2015 |
| WO | 9605233 A1 | 2/1996 |
| WO | WO-2009024350 A2 * | 2/2009 ............. A61K 8/735 |

OTHER PUBLICATIONS

International Search Report and Written Opinion of the International Searching Authority for corresponding application PCT/EP2018/055823 dated Jun. 25, 2018.

GB Search Report for corresponding application GB 1703850.6 dated Nov. 23, 2017.

T. Oka, et al., "Differential Scanning Calorimetry Studies on the Mechanism of Skin-Softening Effect of Sodium Acetylhyaluronate", Elsevier, Polymer, 41, Apr. 19, 2000, pp. 6055-6059.

C. Saturnino, et al., "Acetylated hyaluronic acid", Biomed Research Int., vol. 2014, article 11 Jul. 8, 2014, pp. 1-7.

E. J. Shin, et al.: "Effects of Molecular Weights of Sodium Hyaluronate on the Collagen Synthesis, Anti-inflamation and Transdermal Absorption"; The Journal of the Society Cosmetic Scientists Korea, vol. 42, No. 3, pp. 235-245, 2016.

W.P. Aue, et al.: "Two-dimensional spectroscopy. Application to nuclear magnetic resonance"; The Journal of Chemical Physics, vol. 64, No. 5, 2008.

\* cited by examiner

*Primary Examiner* — Dale R Miller

(74) *Attorney, Agent, or Firm* — Norris McLaughlin PA

(57) ABSTRACT

A skin care composition comprising low molecular weight acetylated hyaluronic acid or its sodium salt having a weight average molecular weight less than 50 kDa, and a degree of acetylation of at least 3.6 is useful in the treatment of the visible effects of age on human skin.

19 Claims, 1 Drawing Sheet

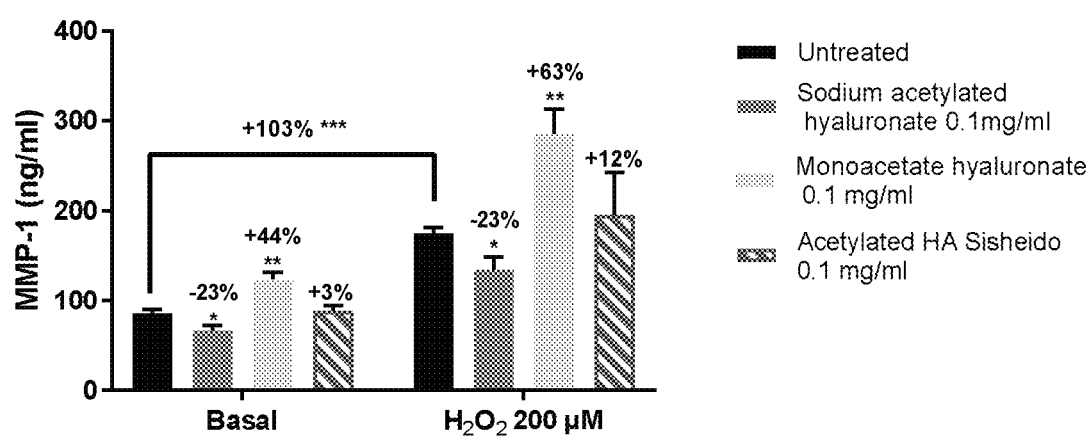

SKIN CARE COMPOSITION COMPRISING ACETYLATED HYALURONIC ACID WITH DEGREE OF ACETYLATION QUANTIFIED BY 2D-MR

This is a Continuation application based on U.S. Ser. No. 16/486710, filed 16.Aug.2019, which in turn was an application filed under 35 USC 371 based on PCT/EP2018/055823, filed 10.Mar.2018, which in turn is based on GB 1703850.6 filed 10.Mar.2017. The present application claims the full priority benefit of these prior applications and herein incorporates by reference the full disclosures of these prior applications.

The invention relates to active ingredients and methods that are useful to reduce the visible signs of aging on human skin. More specifically, the invention relates to the use of acetylated hyaluronic acid or its sodium salt, to inhibit certain matrix-degrading enzymes that are involved in chronological-induced and UV-induced skin deterioration. The invention also relates to novel forms of acetylated hyaluronic acid useful in reducing the visible signs of aging, and to methods of preparing same.

The desire to appear attractive is naturally rooted in modern consumers. Even as the ideal of attractiveness undergoes change over the course of time, it is universally accepted that the condition and appearance of our skin is a significant contributor to an attractive outward appearance.

Today's consumers are offered a multitude of cosmetic products for the care of skin. Generally, these products are in the form of creams and lotions, containing water for moisturizing the skin, and fats and lipids for re-greasing it, and their effects are exerted on the outer-most layer of the skin.

The skin-softening effects of hyaluronic acid are known in the art. However, it is also known that the physical condition of hyaluronic acid in cosmetic preparations deteriorates over time. Acetylated hyaluronic acid has been proposed in EP 0 725 083 as an alternative to hyaluronic acid in that it reportedly has the same skin-softening functions as hyaluronic acid, but does not exhibit the same physical deterioration as the free acid. However, EP 0 725 083 does not suggest or hint at the use of acetylated hyaluronic acid in the treatment of the effects of aging on skin, or its underlying causes.

There are several disclosures of low (EP 0 725 083; and CN 106176286) and intermediate (Saturnino et al. in Biomed Research International, 2014, 921549: "Acetylated hyaluronic acid: enhanced bioavailability and biological studies"; and Oka et al. in Polymer, 41: "Differential scanning calorimetry studies on the mechanism of skin-softening effect of sodium acetylhyaluronate") molecular weight acetylated hyaluronic acid and acetyl hyaluronate with various degrees of acetyl substitution, which may be used in skin care. However, as will be shown below, these products have important drawbacks in comparison to the product of the present invention.

The provision of effective cosmetic preparations useful in the treatment of the causes of skin-aging and thereby reducing the visible signs of aging remains an unmet need.

The structural framework of the skin is referred to as its extracellular matrix. This internal framework comprises a network of inter-meshed polymers, such as collagen and elastin, inside which skin cells are contained. It is responsible for the skin's mechanical properties, including firmness, strength, suppleness and elasticity. The physical signs of skin aging are a reflection of the condition of the skin matrix. More particularly, the weaker and less regular the matrix, the more wrinkles, roughness and sag the skin tends to have.

The skin's extracellular matrix is a precious resource, which in healthy and youthful skin is both produced and consumed. The smoothness, firmness and youthfulness of human skin depend to a large degree on the condition of its matrix, which, in turn, depends on the balance of matrix synthesis and matrix break-down/recycling. The skin's extracellular matrix is composed of collagens (type I collagen being the most prevalent); elastins; and other components such as glycosaminoglycans (GAGs). The matrix is synthesized by fibroblasts in the dermis, and it is subject to remodeling by certain specific enzymes (the matrix metalloproteinases, or MMPs). These enzymes are usually involved in wound—healing, but they are over-expressed during chronological and UV-induced aging, whereupon they promote intense and uncontrolled matrix break-down, which is known to be responsible for the visible signs of aging, such as skin collapse and wrinkle formation. There are around 20 MMPs that are grouped into different categories according to their substrate specificity. Among them are the collagenases, gelatinases, stromelysins, and membrane-type MMPs. MMP-1 is the most well-known collagenase and is involved in the cleavage of structural collagens, such as the type-1 collagen. MMP-3 is a stromelysin that is involved in the cleavage of basement membrane collagens, such as collagen IV.

Matrix proteins are large, structural molecules that have long half-lives (in the order of 70 years in the case of elastin). Consequently, these materials are hardly replenished or renewed over the normal human life-span. As such, there is a progressive alteration and degradation of the matrix that accelerates with age, disrupting and weakening the skin's scaffold and creating the visible signs of aging.

Skin aging is the result of the intrinsic chronological aging process superimposed with environmental factors, predominantly consisting of exposure to ultraviolet radiation. MMP levels rise excessively in the course of normal chronological aging, and the environmental factors act to elevate MMP levels still further. Reducing the levels of MMP enzymes and returning them to normal, youthful levels, which are sufficient to alleviate matrix degradation, and preserve a healthy matrix, may help to reduce or eliminate the visible signs of aging on human skin.

There remains a need to provide methods and cosmetic preparations for application to the skin that can reverse or reduce degradation of the skin's matrix, by inhibiting or reducing elevated levels of matrix-degrading enzymes, such as MMPs, down to balanced levels found in youthful or healthy skin.

The invention relates to the use of acetylated hyaluronic acid or its sodium salt (sodium acetyl hyaluronate) to control the balance of matrix-degrading materials in the skin's extra-cellular matrix, reducing the extent of degradation of essential matrix proteins such as collagen, and to reduce the visible signs of aging (chronologically-induced and environmentally-induced), particularly the prevention or reduction of skin wrinkles and to the production and maintenance of youthful looking skin.

Accordingly, the invention encompasses the following aspects and embodiments:

A method of inhibiting the degradation of the skin's extracellular matrix associated with elevated levels of matrix-degrading enzymes, said method comprising the step of applying to the skin an effective amount of acetylated hyaluronic acid or its sodium salt, in particular in the form of the skin care composition of the present invention.

The method described above, which is a method for reducing the visible signs of skin aging, more particularly a method of preventing or reducing wrinkles.

The method described above, wherein the matrix-degrading enzymes are matrix metalloproteinases, and more particularly the enzymes MMP-1 or MMP-3.

The method described above, wherein acetylated hyaluronic acid or its sodium salt acts to reduce the extent of degradation of collagen in the extra-cellular-matrix, in particular the degradation by metalloproteinases.

A low molecular weight fraction of acetylated hyaluronic acid, or its sodium salt, with a high degree of acetylation, for use in a method described herein.

The acetylated hyaluronic acid, or its sodium salt, described above having a weight average molecular weight of about 50 kDa or less, more particularly about 35 kDa or less, and still more particularly about 30 kDa or less.

The acetylated hyaluronic acid, or its sodium salt, described above, having a weight average molecular weight of about 50 kDa or less, more particularly about 35 kDa or less, and still more particularly about 30 kDa or less, and a polydispersity index that is less than 2.3, more particularly less than 2.0, more particularly less than 1.8, more particularly less than 1.7, more particularly less than 1.6 or less, more particularly less than 1.5, more particularly less than 1.4, and more particularly about 1.3 or less.

The acetylated hyaluronic acid, or its sodium salt, described above having a degree of acetylation that is greater than 3.6, more particularly 3.7 or greater, more particularly 3.8 or greater, more particularly 3.9 or greater, and more particularly still 4.

The acetylated hyaluronic acid, or its sodium salt, described above having a degree of acetylation that is greater than 3.6, more particularly 3.7 or greater, more particularly 3.8 or greater, more particularly 3.9 or greater, and more particularly still 4 determined using quantitative 2D NMR.

A method of preparing low molecular weight acetylated hyaluronic acid or its sodium salt having a weight average molecular weight of 50 kDa or less and an average degree of acetylation of greater than 3.6, comprising the steps of
 (i) selecting low molecular weight hyaluronic acid having a molecular weight of 50 kDa or less, more particularly 35 kDa or less, or still more particularly 30 kDa or less;
 (ii) subjecting it to acetylation conditions, wherein the acetylation conditions preferably comprise the step of reacting the low molecular weight hyaluronic acid with an acetic acid/acetic anhydride mixture in the presence of a strong acid; and
 (iii) isolating the low molecular weight acetylated hyaluronic acid, preferably by precipitation using additive water.

A cosmetic preparation comprising an effective amount of the acetylated hyaluronic acid, or its sodium salt, described above.

A skin care composition comprising low molecular weight acetylated hyaluronic acid or its sodium salt, characterized in that the low molecular weight acetylated hyaluronic acid or its sodium salt has a weight average molecular weight of 50 kDa or less and an average degree of acetylation of greater than 3.6.

The cosmetic preparation, and in particularly the skin care composition, described above, comprising at least one cosmetically acceptable excipient.

These and other aspects of the invention will be better understood in view of the following detailed description of particular embodiments of the invention.

Skin-aging is a term that refers to the changes experienced by the skin with age, whether that is through chronological aging or through exposure to the sun (photo-aging) or through other environmental agents such as tobacco smoke, extreme climatic conditions of cold, heat, or wind, chemical contaminants or pollutants, and includes all the external visible and/or perceptible changes through touch, such as but not restricted to, the development of discontinuities on the skin such as wrinkles, fine lines, furrows, irregularities or roughness, increase in the size of pores, loss of elasticity, loss of firmness, loss of smoothness, loss of the capacity to recover from deformation, sagging of the skin such as sagging cheeks, the appearance of bags under the eyes or the appearance of a double chin, among others, changes to the colour of the skin such as marks, reddening, or the appearance of hyper-pigmented areas such as age spots or freckles among others, anomalous differentiation, hyper-keratinization, elastosis, keratosis, loss of collagen structure and other histological changes of the stratum corneum, of the dermis, or epidermis.

It is known that an elevated level of matrix metalloproteinases (MMPs) is a key factor in skin-aging. MMPs, such as MMP-1 and MMP-3, are involved in matrix degradation, and in particular the degradation of type I collagen, which is the most important type of collagen found in the dermis. During the chronological aging process, as well as a result of UV exposure and exposure to other environmental agents, the production of MMPs increases, leading to dermal degradation, skin collapse, the formation of wrinkles and thus the first visible signs of skin aging.

Surprisingly, it was found that acetylated hyaluronic acid, or its sodium salt, is able to reduce the levels of MMPs, and in particular MMP-1 and MMP-3. It is believed, although the applicant does not wish to be bound by theory, that the lower level of MMPs is a result of down-regulation of genes encoding for these enzymes.

The biological effect of the acetylated hyaluronic acid or its sodium salt of the present invention has been demonstrated in certain gene expression studies performed on the three main cell types present in the skin: fibroblasts, keratinocytes and melanocytes. The biological impact of acetylated hyaluronic acid, or its sodium salt, was also determined by in-vitro protein and functional studies. We have found that it presents a new anti-aging activity linked to limiting matrix degradation and protecting the skin against age signs. The studies are described in more detail herein below in the examples.

By contrast, the acetylated hyaluronic acid described in CN 106176286 (obtained from Bloomage Freda Biopharm Co., Ltd.) was found not to induce any gene response.

The finding that acetylated hyaluronic acid, or its sodium salt, when applied to the skin, can elicit a biological effect that is observable as a reduction in the visible signs of skin aging, such as a reduction in skin-wrinkles enables the skilled person in the art to provide cosmetic preparations for application to the skin of a human subject.

Cosmetic preparations, and in particular skin care compositions, of the present invention contain a cosmetically acceptable amount of acetylated hyaluronic acid or its sodium salt.

A cosmetically effective amount of acetylated hyaluronic acid or its sodium salt is understood to be a non-toxic but sufficient quantity of acetylated hyaluronic acid or the sodium salt to provide the desired effect. With regard to the total weight of a cosmetic preparation, in particular the skin care composition, the acetylated hyaluronic acid or its sodium salt may be present in amounts of about 0.005 to about 5.0 wt %, and more particularly about 0.05 to about 0.5 wt %.

Cosmetic preparations, and in particular skin care compositions, of the present invention may contain one or more cosmetically acceptable excipients. Any excipients commonly used in the preparation of cosmetic preparations for use on the human skin may be employed in the present invention. Suitable excipients include, but are not limited to ingredients that can influence organoleptic properties, penetration of the skin, and the bioavailability of the acetylated hyaluronic acid or it sodium salt. More specifically, they include liquids, such as water, oils or surfactants, including those of petroleum, animal, plant or synthetic origin, such as and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin, and the like.

The cosmetic preparation, and in particular the skin care composition, may be in the form of a liposome composition, mixed liposomes, oleosomes, niosomes, ethosomes, milliparticles, microparticles, nanoparticles and solid-lipid nanoparticles, vesicles, micelles, mixed micelles of surfactants, surfactant-phospholipid mixed micelles, millispheres, microspheres and nanospheres, liposperes, millicapsules, microcapsules and nanocapsules, as well as microemulsions and nanoemulsions, which can be added to achieve a greater penetration of the acetylated hyaluronic acid or its sodium salt.

The cosmetic preparation, and in particular the skin care composition, may be produced in any solid, liquid, or semi-solid form useful for application to the skin topically or by transdermal application. Thus, these preparations of topical or transdermal application include, but are not restricted to, creams, multiple emulsions, such as and not restricted to, oil and/or silicone in water emulsions, water-in-oil and/or silicone emulsions, water/oil/water or water/silicone/water type emulsions, and oil/water/oil or silicone/water/silicone type emulsions, micro-emulsions, emulsions and/or solutions, liquid crystals, anhydrous compositions, aqueous dispersions, oils, milks, balsams, foams, aqueous or oily lotions, aqueous or oily gels, cream, hydro-alcoholic solutions, hydro-glycolic solutions, hydrogels, liniments, sera, soaps, face masks, serums, polysaccharide films, ointments, mousses, pomades, pastes, powders, bars, pencils and sprays or aerosols (sprays), including leave-on and rinse-off formulations.

The finding that acetylated hyaluronic acid or its sodium salt elicits a biological effect was particularly surprising considering that it was not possible to reproduce the effect using unmodified hyaluronic acid or salt, confirming that the activity is related to the acetylation of the free acid form or the salt.

Particularly preferred forms of acetylated hyaluronic acid or its sodium salt for use in the present invention are characterized in that they have a very high degree of acetylation. More particularly, preferred forms of acetylated hyaluronic acid are characterized by an average degree of acetylation of greater than 3.6, more particularly 3.7 or higher, more particularly 3.8 or higher, more particularly 3.9 or higher, and more particularly still 4.

Hyaluronic acid is a polysaccharide consisting of a repeat unit containing N-acetyl glucosamine and glucuronic acid. It can exist in its free-acid or sodium salt form. In its acetylated form, the term "degree of acetylation" is understood as a measure of the number of hydroxyl groups on the polymer repeat unit that are acetylated. Each repeat unit of native hyaluronic acid/salt polymer contains four hydroxyl groups that can be acetylated and the degree of acetylation is a measure of how many of these groups are substituted by an acetyl group.

Measuring the degree of acetylation is particularly challenging using conventional analytical techniques. For example, we found that traditional one dimensional NMR is ineffective because of the coincidence of chemical shifts of the protons that need to be measured.

However, applicant elucidated an analytical method using two dimensional NMR in which the N-acetyl group on the glucosamine moiety of the hyaluronic acid or its sodium salt is used as an internal standard to quantify the acetyl functionality introduced in the acetylation process.

In order to integrate these two types of signals (O-acetyl group and N-acetyl), applicant devised a 2D-NMR method. More particularly, the 2D-NMR method is a hetero-nuclear method (Hetero-nuclear Single Quantum Coherence (HSQC) analysis), measuring a proton signal in one dimension, and the signal from carbon nuclei in the second dimension.

By employing the 2D-NMR technique, applicant found that it was possible to clearly resolve N-acetyl signal, from the signals associated with the O-acetyl groups, allowing the volume integration of these groups, and thus enabling a quantitative determination of the degree of acetylation. The basic scheme of a suitable HSQC experiment is set forth in the following paragraphs:

Analysis of the degree of acetylation is made by a gradient enhanced $^1$H-$^{13}$C HSQC method allowing the volume integration for the cited acetyl groups in a quantitative manner.

The $^1$H-$^{13}$C coupling constant provides information concerning the connectivity of atoms in a molecule, and in NMR spectroscopy it is responsible for the appearance of many signals in a spectrum. The integration volumes of cross-peaks in a HSQC experiment are modulated by the $^1$H-$^{13}$C coupling constant $^1J_{C,H}$. However, cross-peaks arising from different coupling constants usually do not permit quantitative integration. However, applicant found advantageously that in the case of the current analytic method, $^1J_{C,H}$(N-acetyl) was substantially equal to $^1J_{C,H}$(O-acetyl), allowing a quantitative analysis.

As in standard 1D-NMR quantifications, a sufficient relaxation delay may be provided in order to ensure that both N-acetyl and O-acetyl protons have time to relax from one scan to another, in order to stay in quantitative conditions. Additionally, in order to restrain differentiated $T_2$ relaxation between the N- and O-acetyl species of interest during the sequence, the two delays given by $(4\times J_{C,H})^{-1}$ within the INEPT (Insensitive Nuclei Enhanced by Polarization Transfer) transfer of the HSQC were held as short as possible, e.g. for about 1.5 milliseconds.

The 2D-NMR measurements can be carried out on any high-field instrument available in the art. An example of a suitable instrument is a high-field NMR instrument equipped with a Cryoprobe probehead, more particularly a Bruker Avance III 600 MHz, MicroCryoprode TCI 1.7 mm.

Samples for analysis may be prepared as 1.2 mg of acetylated hyaluronic acid, or its sodium salt, dissolved in 50 ml $D_2O$ 99.96% D. The sample solution can be transferred in the NMR tube (1.7 mm, Bruker) for measurement. Typical measurement parameters include: T=60° C.; number of scans=4; dummy scans=32; recovery delay=10s; acquisition time=177 ms; spectral width ($^1$H)=6.0 ppm; spectral width ($^{13}$C)=110 ppm; $^1$H-pulse offset=3.5 ppm; $^{13}$C-pulse offset=60 ppm; time domain ($^1$H)=1272; time domain ($^{13}$C)=256. Software for data acquisition and processing, including cross-peak integration is TopSpin 3.0 (Bruker).

In particular, this 2D-NMR technique allowed for distinguishing the acetylated hyaluronic acid or sodium salt of the present invention from the product described in EP 0 725 083 and sold by Shiseido: Shiseido's acetyl hyaluronate had an average acetylation degree of only about 3.6. This is important, as Shiseido's product also proved inferior to the product of the present invention with respect to anti-aging activity, as will be shown in Example 5 below.

The acetylated hyaluronic acid or sodium salt used in methods and cosmetic preparations, in particular skin care compositions, of the present invention is a low molecular weight acetylated hyaluronic acid or sodium salt thereof. The term "low molecular weight" refers to polymeric material having a weight average molecular weight (Mw) that is 50 kDa or less, more particularly 35 kDa or less, more particularly about 30 kDa or less, more particularly 25 kDa or less, more particularly 20 kDa or less, more particularly 15 kDa or less, and still more particularly about 10 kDa to 15 kDa, for example 13 kDa+/−1 kDa.

The molecular mass of the acetylated hyaluronic acid or its sodium salt polymer fractions should be rather narrowly dispersed. Preferably, the acetylated hyaluronic acid or its sodium salt has a polydispersity index (Mw/Mn) that is less than 2.0, more particularly less than 1.8, more particularly less than 1.7, more particularly less than 1.6 or less, more particularly less than 1.5, and still more particularly about 1.4 or less.

For comparison, the products described in EP 0 725 083 (obtained from Shiseido) and CN 106176286 (obtained from Freda) were analyzed by SEC-HPLC (size-exclusion chromatography and high performance liquid chromatography) using light-scattering detection. The following results were obtained:

| | Weight average molecular weight (Mw) | polydispersity index (Mw/Mn) |
|---|---|---|
| Shiseido product | 34'958 Da | 1.560 |
| Freda product | 45'676 Da | 1.580 |
| Product of the present invention | 11'721 Da | 1.485 |

The intrinsic viscosity of the acetylated hyaluronic acid or its sodium salt is preferably less than 0.3 dl/g (30 cm$^3$/g), and more particularly 0.245 dl/g (24.5 cm$^3$/g)+/−0.01 dl/g (1 cm$^3$/g).

The foregoing physical parameters can be measured by HPLC Size Exclusion Chromatography. A suitable instrument is a Viscotek GPC max VE2001, equipped with Triple Detection Parameters (Viscotek TDA 305): refractometer, capillary viscosimeter and light scattering.

Light scattering measurements characterize particle size distribution by measuring the angular variation in intensity of light scattered as a laser beam passes through a dispersed particulate sample. Large particles scatter light at relatively smaller angles relative to the laser beam and small particles scatter light at relatively larger angles. The angular scattering intensity data is then analyzed to calculate the size of the particles responsible for creating the scattering pattern, using the Mie theory of light scattering. The particle size is reported as a volume equivalent sphere diameter. Size Exclusion Chromatography (SEC) is an analytical technique that separates dissolved macromolecules by size based on their elution from columns filled with a porous gel. When SEC is coupled with light scattering, viscometer and concentration detectors (known as triple detection), one can measure molecular weight, molecular size and intrinsic viscosity.

In a typical measurement protocol, the acetylated hyaluronic acid or its sodium salt (0.2 g) is solubilized in TBS buffer (100 ml) by stirring for 1 h at 45° C., before storing the solution for an additional 2 h at room temperature under stirring to fully hydrate the polymer. The solution is filtered through a 0.2 μm nylon syringe filter. The solution is then injected in HPLC SEC LALS (100 μl). Analysis is performed at 0.35 ml/min with TBS buffer pH 7 at 35° C. A typical run time is 90 minutes and a typical injection volume 100 μl.

The low molecular weight acetylated hyaluronic acid or its sodium salt is a preferred material for use in methods and cosmetic preparations, in particular skin care compositions, of the present invention. The use of low molecular weight material is believed to be advantageous because of its superior skin penetration properties compared with higher molecular weight fractions.

Hyaluronic acid or its sodium salt can be acetylated according to techniques known in the art.

In a suitable method, hyaluronic acid is dissolved in a mixture of acetic anhydride and acetic acid. Thereafter, a strong acid, such as sulphuric acid is added to the solution, to effect acetylation. Such a method is described in EP 0 725 083 B1.

In an embodiment of the invention, the mixing ratio (wt/wt) of acetic acid to acetic anhydride may vary within the range of 1:4 to 1:1. The mixing ratio (wt/wt) of strong acid to hyaluronic acid may be 1:5 to 1:1.

The applicant found in a surprising manner that a particularly high degree of acetylation can be achieved if the acetylation reaction is carried out using low molecular weight hyaluronic acid as the starting material. Without wishing to be bound by theory, it is believed that low molecular weight hyaluronic acid is more easily and more extensively acetylated than high molecular weight starting material because the hydroxyl groups are less sterically hindered in low molecular weight starting material and therefore more easily acetylated. For this reason, it is preferred that the acetylated hyaluronic acid or its sodium salt of the present invention is prepared using low molecular weight hyaluronic acid or sodium salt as the starting substrate.

Accordingly, in another aspect of the present invention, there is provided a method of acetylating hyaluronic acid, wherein the hyaluronic acid starting material is a low molecular weight fraction with a weight average molecular weight of about 50 kDa or less, more particularly of about 35 kDa or less, and still more particularly of about 30 kDa or less.

By employing a hyaluronic acid substrate having the aforementioned low molecular weight, it is possible to prepare highly acetylated hyaluronic acid, or its sodium salt, having a weight average molecular weight (Mw) of 50 kDa or less, more particularly 35 kDa or less, more particularly about 30 kDa or less, more particularly 25 kDa or less, more particularly 20 kDa or less, more particularly 15 kDa or less, and still more particularly about 10 kDa to 15 kDa, for example 13 kDa+1-1 kDa. These low molecular weight forms of acetylated hyaluronic acid and sodium acetyl hyaluronate form additional aspects of the present invention.

A method of preparing the low molecular weight acetylated hyaluronic acid or its sodium salt, said method comprising the steps of selecting a low molecular weight hyaluronic acid having a weight average molecular weight of about 50 kDa or less, more particularly about 35 kDa or less, and still more particularly about 30 kDa or less, and reacting it under acetylating conditions, for example, those conditions describe herein, forms yet another aspect of the invention.

By means of the synthetic procedure described above, a crude reaction mixture containing the desired acetylated hyaluronic acid is obtained, from which the acetylated hyalouronic acid is preferably isolated and purified.

Accordingly, the invention provides in another of its aspects a method of isolating low molecular weight acetylated hyaluronic acid from a crude reaction mixture containing the low molecular weight acetylated hyaluronic acid in solution.

In a particular embodiment of the invention, the method of isolating the low molecular weight acetylated hyaluronic acid comprises the step of precipitating it from solution using additive water.

The characteristic low molecular weight of the acetylated hyaluronic acid enables the precipitation step to be carried out using additive water, rather than an additive volatile organic solvent. This is contrasted with prior art processes that employ additive volatile organic solvents, such as acetone, to precipitate sodium salts of acetylated hyaluronic acid out of a crude reaction mixture.

Given the difficulty of removing all of the organic solvent during work-up, sodium salts of hyaluronic acid formed according to prior art processes can contain residues of the volatile solvent, which can be undesirable. A significant advantage of the present invention is that low molecular weight acetylated hyaluronic acid can be obtained that is free of volatile organic solvents, such as acetone.

Low molecular weight acetylated hyaluronic acid that is free of residues of volatile organic solvent forms another aspect of the invention.

Furthermore, the low molecular weight acetylated hyaluronic acid, free of volatile organic solvent, can be further converted to its sodium salt, in accordance with a method described herein below, and the sodium salt of the low molecular weight acetylated hyaluronic acid, free of volatile organic solvents, forms an additional aspect of the present invention.

Prior to the precipitation step, it may be desirable to remove, at least partially, unconsumed acetic acid and acetic anhydride from the reaction mixture. Acetic acid is a solvent for the low molecular weight acetylated hyaluronic acid, and its partial removal, along with the acetic anhydride, facilitates the precipitation of the low molecular weight acetylated hyaluronic acid by enabling the precipitation step to be carried out with relatively small volumes of additive water.

The acetic acid/acetic anhydride mixture can be removed by distillation, leaving the crude reaction mixture in the form of a viscous paste consisting mainly of the desired low molecular weight acetylated hyaluronic acid. Water is then added to this crude mixture to effect precipitation. The distilled acetic acid/acetic anhydride mixture may be collected and recycled.

In a preferred embodiment of the invention, the amount of additive water is 1 to 5 weight equivalents, more particularly 2 to 4 weight equivalents per one part of the crude reaction mixture containing the desired acetylated hyaluronic acid. As water is added to the reaction mixture, any residual acetic anhydride is hydrolyzed. The strongly exothermic hydrolysis is preferably performed in such a manner that the temperature of the reaction mass does not exceed 40° C.

Removal of acetic acid/acetic anhydride may be carried out by distillation. Prior to the distillation step, it may be desirable to neutralize any strong acid in the reaction mixture to avoid contacting the acetylated hyaluronic acid with the strong acid under reflux conditions, which may lead to the emanation of undesirable discolouration. The adjustment of the pH of the crude reaction mixture before precipitation is therefore a preferred process step in an isolation and purification process according to the invention.

Accordingly, in another aspect of the invention, there is provided a method of isolating the low molecular weight acetylated hyaluronic acid from a reaction mixture containing the low molecular weight acetylated hyaluronic acid in solution, said method comprising the step of precipitating the low molecular weight acetylated hyaluronic acid from the solution at a pH of 5 to 8 using additive water.

In a particular embodiment of the invention, there is provided a method of isolating the low molecular weight acetylated hyaluronic acid from a reaction mixture containing the low molecular weight acetylated hyaluronic acid in solution, said method comprising the step of adjusting the pH of the reaction mixture to a pH in the range of 5 to 8 and precipitating the low molecular weight acetylated hyaluronic acid from this solution using additive water.

For the purpose of the present invention, pH adjustment may be carried out using a suitable buffering agent, for example phosphates, acetates and citrates known for such purpose, and more particularly, buffering is carried out by the addition of an effective amount of sodium acetate.

The precipitated acetylated hyaluronic acid may be separated and isolated from other components of the reaction mixture by filtration over a suitable filter, such as any fine mesh textile filter known for such purpose.

The precipitated low molecular weight acetylated hyaluronic acid may be subjected to additional work-up procedures after precipitation. For example, it may be washed with water in order to remove any traces of water-soluble impurities, before drying the precipitated material to afford the low molecular weight acetylated hyaluronic acid in the form of a bright, white free-flowing powder with no or practically no yellowish hue.

The low molecular weight acetylated hyaluronic acid may be used in this form in the methods and cosmetic preparations, in particular skin care compositions, of the present invention.

At this stage, it might also be desirable to subject the acetylated hyaluronic acid to further work-up procedures, such as a bleaching or polishing step to remove any unwanted yellow colouration using, for example, activated carbon. The purified acetylated hyaluronic acid may thereafter be dried, optionally under vacuum, to provide acetylated hyaluronic acid in a form suitable for use in methods and cosmetic preparations of the present invention without further modification.

Alternatively, it may be desirable to convert the low molecular weight acetylated hyaluronic acid to its sodium salt.

The acetylated hyaluronic acid of the present invention may be converted to its corresponding sodium salt by means of a neutralization step.

Neutralization may be carried out by adding an aqueous source of sodium ions, such as sodium hydroxide, sodium acetate or any other suitable sodium-ion-containing base to an aqueous solution or suspension of the low molecular weight acetylated hyaluronic acid.

The neutralization step may be carried out at a temperature of 0 to 30° C., and the reaction time may vary within the range of 0.5 to 12 hours.

During the neutralization, it is desirable that the base, for example sodium hydroxide, is added to the solution or suspension of the low molecular weight acetylated hyaluronic acid slowly in order that appreciable concentrations of the base do not build-up, and the pH does not exceed about 9, more particularly about 8, more particularly about 7.5, more particularly about 7, and more particularly still about 6.5. In this way, no undesirable by-products are created and the emanation of undesirable discolouration is avoided.

The course of the neutralization reaction may be conveniently followed by following the pH of the reaction mixture, and a neutralized solution of the corresponding low molecular weight sodium acetyl hyaluronate is obtained when the pH reaches 6.5+/−0.5.

The low molecular weight sodium acetyl hyaluronate solution, which forms another aspect of the invention, may be used in this form in the methods and cosmetic preparations, in particular skin care compositions, of the present invention without further modification. However, if it is desired to use the sodium acetyl hyaluronate solution as a raw material in said compositions and methods, it is desirable to incorporate into the solution a suitable antimicrobial agent, which agents are well known in the art.

Alternatively, the low molecular weight sodium acetyl hyaluronate may be further processed to render it in solid form, more particularly a powder form.

Prior art methods for isolating sodium acetyl hyaluronate in its solid form comprises the step of precipitating it from an aqueous acetone solution using neat acetone. However, isolating and purifying it in this way can leave residues of volatile organic solvent in the finished product, and these solvents should generally be avoided as far as possible (or removed where appropriate) in order to comply with product specifications and other quality characteristics that may typically be required of raw materials intended for use in the cosmetics industry.

Still further, owing to the high solubility of the low molecular weight sodium acetyl hyaluronate in water, in volatile organic solvents, as well as in mixtures thereof, it cannot be provided in solid form by precipitation.

Another aspect of the present invention is therefore based on the object of providing a method for the production of volatile organic solvent-free low molecular weight sodium acetyl hyaluronate in a solid form, and preferably a powder form, which is bright white, free-flowing and easy to handle.

Applicant achieved these objects and provides a method of converting an aqueous solution of the low molecular weight sodium acetyl hyaluronate into powder form, said method comprising the step of dehydrating the low molecular weight sodium acetyl hyaluronate solution. The dehydration step may be carried out by known techniques, such as lyophilization. More preferably, however, the dehydration step is carried out by spray drying.

Accordingly, the invention provides in another aspect a method of dehydrating a liquid aqueous medium, and in particular a solution, comprising sodium acetyl hyaluronate, in particular, sodium acetyl hyaluronate formed according to a process described herein.

In an embodiment of the invention, there is provided the method described above, wherein said method comprises the steps of atomizing the liquid aqueous medium as droplets into a drying chamber maintained under conditions causing evaporation of the liquid aqueous medium to form particles of sodium acetyl hyaluronate.

In a more particular embodiment, the inlet temperature of the spray drying chamber is about 150° C., and the outlet temperature of the spray-drying chamber is about 70° C. or less.

In a still more particular embodiment, air is pumped into the drying chamber such that the drying chamber outlet temperature is reduced to about 40 to 50° C.

Spray-dried sodium acetyl hyaluronate, which forms another aspect of the present invention, exhibits desirable properties, such as high bulk density, shape and flowability, which make the product easy to handle transport and use. The avoidance of a low density and dusty product is a particular advantage of spray-dried sodium acetyl hyaluronate.

Spray-dried sodium acetyl hyaluronate is formed with sufficient whiteness and clarity that it is eminently suitable for use in products intended for cosmetic applications, and in particular for skin care compositions.

The spray-dried product formed according to a process described above forms yet another aspect of the invention.

Both the low molecular weight acetylated hyaluronic acid and the low molecular weight sodium acetyl hyaluronate are easily incorporated into cosmetic preparations, and in particular skin care compositions. Owing to their very low molecular weight and their powdered physical form, they are not stringy or lumpy, and can be easily dissolved or suspended in aqueous media and mixed into cosmetic bases.

Furthermore, since highly coloured ingredients may be unacceptable as raw materials for manufacturers of cosmetic preparations, it is highly advantageous that both the low molecular weight acetylated hyaluronic acid and the low molecular weight sodium acetyl hyaluronate can be prepared as white powders with no, or substantially no, yellowish hue, and which do not alter or impair the colour tone of any cosmetic preparation into which they might be incorporated, irrespective of the amount of material employed in the cosmetic preparation.

When finishing the work-up of acetylated hyaluronic acid or its sodium salt, one can employ a bleaching or polishing step whereby slight discolouration is removed using a suitable bleaching agent, such as a clay or a form of activated carbon. However, such steps are not particularly effective to decolourize such products if those products are already highly discoloured as a result of the synthetic process.

It is a characteristic of the present invention that the methods of preparation and isolation described herein provide the low molecular weight acetylated hyaluronic acid and low molecular weight sodium acetyl hyaluronate as products that are in the form of white powders of sufficient brightness and clarity that, should a bleaching or polishing step be carried out, it is able to effectively decolourize the products.

More particularly, the methods of preparation and isolation describe herein provide low molecular weight acetylated hyaluronic acid and low molecular weight sodium acetyl hyaluronate as products that are in the form of white powders, each having an L* value of 90 or more; and a b* value, which is less than 8, wherein L* and b* values represent the CIELAB system's chromaticity coordinates.

The lightness and hue of a powder can be characterized by CIELAB chromaticity coordinates L* a* b* according to colorimetric methods known in the art. The L* value is a value specifying the lightness of a substance and is indicated by a value between 0 and 100. An L* value of 100 indicates the brightest state (completely white), and an L* value of 0 indicates the darkest state (completely black). The b* value specifies the blue-yellow hue of a substance. The larger is the b* value, the higher is the degree of yellowness. The smaller is the b* value, the higher is the degree of blueness.

Both the L* value and the b* value may be measured using any suitable commercially available spectrophotometer, such as the Minolta CM3500d. The spectrophotometer should be powered up for at least one hour before making a measurement. A glass container provided therefor should be half filled with the solid product to be measured taking care to ensure that the bottom of the container is fully covered by the product. Thereafter, the filled container should be placed in the sample stand provided therefor. The sample key on the instrument should be pressed and the L* and b* values read off the display panel. Before taking any readings, the instrument should be calibrated for the zero and 100% reflection by placing black and white objects provided therefor on the window of the instruments optical sensor.

There now follows a series of examples that serve to further illustrate the invention.

EXAMPLE 1: METHOD FOR MANUFACTURING SODIUM ACETYL HYALURONATE

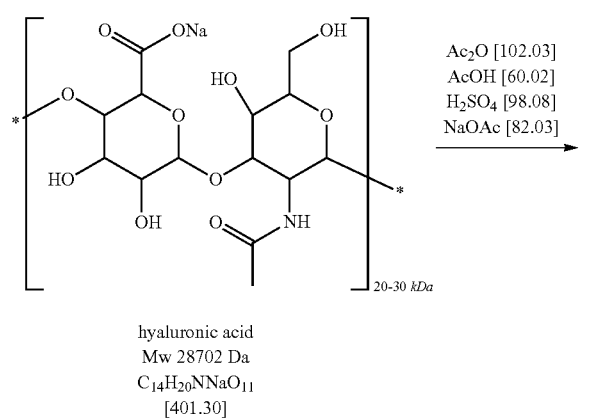

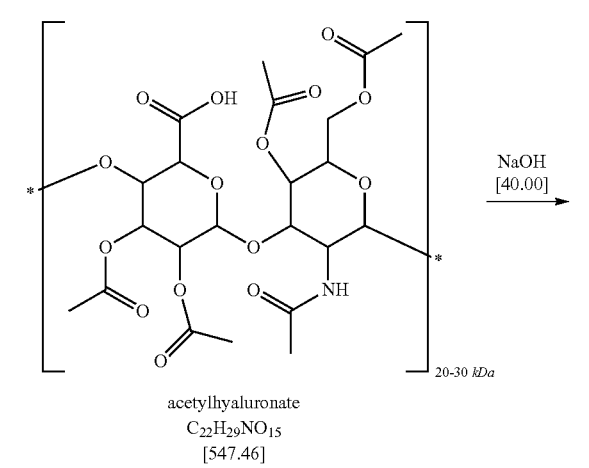

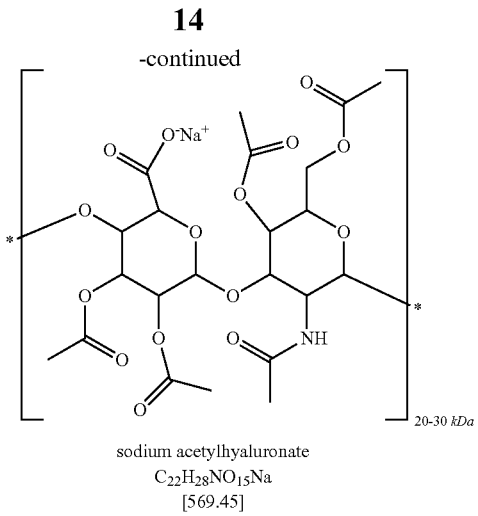

A 5 l reactor was flushed with nitrogen and charged with hyaluronic acid (Renovhyal™ manufactured by Soliance, molecular weight 10-50 kDa; 300 g, 0.7 mol). Commercial grade acetic anhydride (2160 g, 21.2 mol) and acetic acid (525 g, 8.7 mol) were added and the temperature of the suspension was set to 25° C. Sulfuric acid 96% (194 g, 1.9 mol) was added over the period of 10 minutes. The temperature was maintained at 25° C. by internal control. Stirring was continued for 15 hours. The internal control was turned off and sodium acetate (154 g, 1.9 mol) was added while stirring. The temperature rose to 35° C. and stirring was continued for 30 minutes. The reactor was evacuated to 40 mbar and the jacket temperature was set to 50° C. Over the period of 5 hours a mixture of acetic anhydride and acetic acid was removed by distillation (1343 g). The remaining slightly pasty but still stirrable reactor content was cooled to room temperature and water (5500 ml) was added (very carefully at first), maintaining the temperature of the mixture below 50° C. at all times. Gradually a fine, white suspension formed. The solids were isolated by filtration and washed with water (10 l). The solids were then re-suspended in water (700 ml) and the mixture was neutralized (pH 6.5) by the addition of 1M NaOH (600 ml) to afford a solution of sodium acetyl hyaluronate (1520 g, c=0.11 g/g). The solution was submitted for spray-drying to afford sodium acetyl hyaluronate (175 g, 0.3 mol, 44% yield) as a fine, free flowing powder. Analysis by HSQC-NMR experiment indicated an acetylation degree of 3.9.

EXAMPLE 2: METHOD FOR ISOLATING SODIUM ACETYL HYALURONATE BY SPRAY-DRYING TECHNIQUE

Spray drying of an aqueous 11% sodium acetyl hyaluronate solution was carried out using a GEA VERSATILE-SD' 6.3 spray dryer, equipped with a rotary atomizer, using the following parameters:
Feed temperature: 15° C.
Inlet temperature: 150° C.
Outlet temperature: 70° C.
Feed rate: 20 kg/h
Fan speed: 400 kg air/h
Wheels speed: 12000 rpm
A white, free-flowing powder of sodium acetyl hyaluronate was obtained.

EXAMPLE 3: CYTOTOXICITY

Preliminary cytotoxic evaluations of sodium acetyl hyaluronate on fibroblasts and melanocytes were performed by an MTT (3-(4,5-dimethylthiazol-2-yl)-2,5-diphenyltetrazolium bromide) assay test. Briefly, cells were seeded in 96-well culture plates and treated with sodium acetyl hyaluronate at different concentrations of 10, 5, 1, 0.5, 0.1, 0.05, 0.01, and 0.005 mg/ml, respectively, for 24 h and 48 h. Cytotoxicity was evaluated by MTT solution (5 mg/ml diluted at 1/6 in phosphate buffered saline (PBS)). Plates were incubated during 4 h at 37° C. protected from light. The insoluble purple Formazan product was dissolved in 50 µl of DMSO and the optic density was read at 560 nm with a microplate reader (TECAN).

TABLE 1

Cytotoxicity evaluation performed by MTT test on fibroblasts and melanocytes

|  | Fibroblast | | Melanocytes | |
| --- | --- | --- | --- | --- |
| Sodium acetyl hyaluronate | 24 h | 48 h | 24 h | 48 h |
| 10 mg/ml | 67 | 45 | 77 | 83 |
| 5 mg/ml | 74 | 66 | 82 | 90 |
| 1 mg/ml | 89 | 84 | 84 | 91 |
| 0.5 mg/ml | 87 | 93 | 88 | 94 |
| 0.1 mg/ml | 100 | 107 | 93 | 93 |
| 0.05 mg/ml | 109 | 110 | 91 | 91 |
| 0.01 mg/ml | 105 | 112 | 96 | 96 |
| 0.005 mg/ml | 99 | 120 | 88 | 102 |

Regarding the impact of sodium acetyl hyaluronate on fibroblasts in terms of cytotoxicity, it only induced cytotoxicity at concentrations of 10 and 5 mg/ml. Below these doses, no effect was observed.

Regarding its impact on melanocytes, only the concentration 10 mg/ml of sodium acetyl hyaluronate showed a cytotoxic effect. Below this dose, there was no effect on melanocytes (table 1).

The optimal concentration that can be used without inducing toxic effects on each cell type was determined as 0.1 mg/ml for fibroblasts and 0.5 mg/ml for melanocytes. These concentrations were used during the biological investigations.

EXAMPLE 4: TRANSCRIPTOMIC EVALUATION

In order to identify the potential biological activity of sodium acetyl hyaluronate, a transcriptomic in vitro analysis was performed on two cell types present in the skin including melanocytes and fibroblasts. It was studied on 128 genes distributed on two transcriptomic plates. A first plate was specific for dermis function with many genes involved in extracellular matrix, matrix remodelling, oxidation defences, stress responses, wound healing and other biological functions. A second plate was specific for skin pigmentation functions with the most important genes involved in melanin synthesis, melanosomes formation and maturation and other functions linked to melanocytes.

The transcriptomic analysis was performed by Rt-qPCR (Real Time-quantification Polymerisation Chain Reaction) using TaqMan assays in triplicate for each cell types. Briefly after 24 h of cell stimulation at 0.1 mg/ml for fibroblast and 0.5 mg/ml for melanocytes, total RNA was extracted by the Trizol method. Total RNA was quantified by spectrometer and concentrations were adjusted to 400 ng/µl. The quality of RNA was verified by migration on agarose gel. Total RNA was retro-transcripted to cDNA using a cDNA Verso kit following the supplier's recommendations. The retro-transcription was validated by classical PCR targeting housekeeping gene: RPL32 gene. cDNA was then used to perform RT-qPCR where 10 ng of cDNA was deposited per well using a TaqMan assay.

Results obtained are represented in the table 2 below. An induction of more than 1.3 fold (positive or negative) in comparison with the untreated condition is considered to be indicative of a biological modification.

TABLE 2

Genes that are significantly modulated by sodium acetyl hyaluronate on fibroblast (dermis) and melanocytes (pigmentation). $p < 0.05$ *

|  | Gene name | Fold induction |
| --- | --- | --- |
| Dermis (NHDF) | MMP-1 | −1.51 (*) |
|  | MMP-3 | −1.35 (*) |
| Pigmentation (NHM) | HPS4 | +1.82 (*) |
|  | MITF | +1.28 (*) |
|  | ENDR6 | +1.33 (*) |

EXAMPLE 5: IMPACT OF SODIUM ACETYL HYALURONATE ON FIBROBLASTS (DERMIS)

Regarding the results concerning dermis, MMP-1 and MMP-3 are two matrix metalloproteinases involved in matrix degradation, such as type I collagen, which is the most important collagen present in the dermis.

During the aging, the production of MMPs increases leading to intradermal matrix degradation that promotes the skin collapse and wrinkle formation. They represent the first visible signs of skin aging.

This phenomenon can be accelerated by external factors such as UV exposure. Indeed, UV induces oxidative stress in the skin that is responsible for a significant increasing of MMPs release, which in turn promotes the premature aging of the skin by severe matrix degradation.

The transcriptomic results suggest that sodium acetyl hyaluronate could limit this effect by down-regulation of MMP-1 and MMP-3 (table 2).

A specific in-vitro aging model able to overexpress MMP-1 and MMP-3 by the oxidative stress ($H_2O_2$ 100 µM-200 µM for 2 h) on fibroblasts was developed. Briefly, fibroblasts were pre-conditioned with sodium acetyl hyaluronate (0.1 mg/ml) in basal medium for 2 h before the induction of oxidative stress. After the oxidative stress, fibroblasts were incubated 48 h in basal medium at 37° C. permitting MMPs to accumulate in the culture medium. The quantity of MMP-1 and MMP-3 released from supernatants was then estimated by the multiplex method using Luminex technology (principle of ELISA on beads).

MMP-1 Release:

TABLE 3

Impact of sodium acetyl hyaluronate on MMP-1 release induced by oxidative stress in vitro on fibroblasts (expressed in Arbitrary Units).

| MMP-1 | No active | Sodium acetyl hyaluronate (0.1 mg/ml) | Sodium hyaluronate (0.1 mg/ml) |
| --- | --- | --- | --- |
| 100 µM $H_2O_2$ | 1.48 | 0.80 (*; 46%) | 1 (ns; 32%) |
| 200 µM $H_2O_2$ | 1.95 | 1.17 (*; −40%) | 1.61 (ns; −17%) |

* = $p < 0.05$;
ns = not significant.
The percentage values shown in parentheses reflect the amount of inhibition induced by sodium acetyl hyaluronate or sodium hyaluronate relative to no active being present.

It was demonstrated that sodium acetyl hyaluronate significantly decreased the MMP-1 secretion mediated by oxidative stress at the protein level. Conversely, it was found that sodium Hyaluronate was not able to reproduce this effect, confirming that the effects observed were due to the acetylation modification (table 3).

Comparative Study on MMP-1 Release:

For comparison, the effects of (a) the product of the present invention, (b) monoacetate hyaluronate and (c) acetylated hyaluronate according to EP 0 725 083 (from Shiseido; average acetylation degree about 3.6; MW about 100 kDa) on MMP-1 were investigated according to the following procedure:

Fibroblasts from abdominal biopsy of a Caucasian female (age 26) were seeded in 12-well plates at 200'000 cells/well in 1 ml of complete medium (ZenBio, ref. DF-1). 24 h after plating, the complete medium was replaced by basal medium without serum (Zen-Bio, ref. DF-2). After 24 h of culture in basal medium, the cells were pre-incubated with the test products at 0.1 mg/ml for 2 h at 37° C. and were then exposed to oxidative stress ($H_2O_2$ 200 μM) for 2 h at 37° C. The culture medium was replaced by basal medium and cells were incubated for another 48 h at 37° C. Supernatant was collected and stored at −80° C. until analysis.

MMP-1 quantification was performed using the RayBio® Human MMP-1 ELISA kit, an in vitro enzyme-linked immunosorbent assay for the quantitative measurement of human MMP-1 pro and active forms in serum, plasma, and cell culture supernatants. This assay employs an antibody specific for human MMP-1 coated on a 96-well plate. Standards and samples are pipetted into the wells and MMP-1 present in a sample is bound to the wells by the immobilized antibody. The wells are washed and biotinylated antihuman MMP-1 antibody is added. After washing away unbound biotinylated antibody, HRP conjugated streptavidin is pipetted to the wells. The wells are again washed, a TMB (3,3',5'5'-tetramethylbenzidine) substrate solution is added to the wells and color develops in proportion to the amount of MMP-1 bound. The Stop Solution changes the color from blue to yellow, and the intensity of the color is measured at 450 nm.

MMP-1 was measured after a 1/100 dilution of samples, in triplicate. Standard curve was done in duplicate. From MMP-1 standard concentrations of 18'000, 6'000, 2'000, 666.7, 222.2, 74.07 and 24.69 pg/ml, a four-parameter logistic regression was calculated.

The results are shown in FIG. 1.

In basal condition, it was found that only the sodium acetylated hyaluronate of the present invention (a) induced a significant inhibition of MMP-1 production (−23%). The monoacetate hyaluronate (b) did not reproduce the effect and even showed an opposite effect with an increase of MMP-1 production (+44%). The acetylated hyaluronic acid from Sisheido (c) had no significant effect on MMP-1 release in this experimental condition (+3%).

Under oxidative stress mediated by a $H_2O_2$ (without acetylated hyaluronate treatment) in order to reproduce the effect of aging, a significant over-production of MMP-1 was observed (+103%), which validated the experiment.

A pre-incubation with the sodium acetylated hyaluronate of the present invention (a) induced a significant reduction of stress-mediated MMP-1 production, while the both other products showed an inverse effect with +63% and +12% for monoacetate hyaluronate (b) and acetylated hyaluronic acid from Sisheido (c), respectively.

In conclusion, only the sodium acetylated hyaluronate of the present invention (a) presents an efficient activity on the inhibition MMP-1 release in basal and in presence of oxidative stress (aging like).

MMP-3 Release:

TABLE 4

Impact of sodium acetyl hyaluronate on MMP-3 release induced by oxidative stress in vitro on fibroblasts (expressed in Arbitrary Units).

| MMP-3 | No active | Sodium acetyl hyaluronate (0.1 mg/ml) | Sodium hyaluronate (0.1 mg/ml) |
| --- | --- | --- | --- |
| 100 μM $H_2O_2$ | 1.25 | 0.91 (*; −7%) | 1.03 (ns; 18%) |
| 200 μM $H_2O_2$ | 1.83 | 1.15 (*; −37%) | 1.39 (ns; −24%) |

*= $p < 0.05$;
ns = not significant.
The percentage values shown in parentheses reflect the amount of inhibition induced by sodium acetyl hyaluronate relative to no active (no sodium acetyl hyaluronate).

It was demonstrated that sodium acetyl hyaluronate significantly decreased MMP-3 secretion mediated by oxidative stress at the protein level. Conversely, it was found that sodium hyaluronate was not able to reproduce this effect, confirming that the effect observed was due to the acetylation modification (table 4).

Fluorescence Measurements

MMPs are released under two forms including inactive pro-form (pro-MMP) and active form with the pro-peptide cleaved (MMP). Only the active MMPs are able to induce collagen degradation. DQ-type I collagen that is a type I collagen fluorescent linked to a quencher was used. When it is degraded it promotes the quencher release and fluorescence emission. Finally, the emitted fluorescence which is proportional to collagen degradation was measured. This experiment was performed exactly under the same experimental conditions that were used to quantify the secretion of MMP-1 and MMP-3. Briefly, supernatant was incubated with DQ-collagen for 4 h at room temperature and the fluorescence was measured by Microplate Reader (TECAN) with excitation wavelength 495 nm and emission wavelength 515 nm.

TABLE 5

Impact of sodium acetyl hyaluronate on type I collagen degradation after oxidative stress in vitro on fibroblast (expressed in Arbitrary Units).

| | No active | Sodium acetyl hyaluronate (0.1 mg/ml) | Sodium hyaluronate (0.1 mg/ml) |
| --- | --- | --- | --- |
| 100 μM $H_2O_2$ | 157% | 130% (ns; −17%) | 160% (ns; +1%) |
| 200 μM $H_2O_2$ | 157% | 91% (*; −42%) | 149% (ns; −5%) |

* = $p < 0.05$;
ns = not significant.
The percentage values shown in parentheses reflect the amount of inhibition induced by sodium acetyl hyaluronate or sodium hyaluronate relative to no active being present.

It was observed that sodium acetyl hyaluronate decreased the DQ-collagen degradation like observed by the decreasing of fluorescence level (table 5). These results demonstrated that sodium acetyl hyaluronate limits the release of active forms of MMP-1 and MMP-3 responsible of DQ-collagen degradation. Overall, these in vitro results proved that sodium acetyl hyaluronate possesses an anti-aging activity through an impact on matrix remodelling which is involved in the visible signs of skin aging. Indeed, it limits this by a down-expression of MMP-1 and MMP-3 that control the matrix degradation such as type I collagen. In addition, sodium hyaluronate was not able to promote the same results confirming that the bioactivity is linked to the acetylated modification (table 5).

EXAMPLE 6: IMPACT OF SODIUM ACETYL HYALURONATE ON MELANOCYTES (MELANOCYTES)

Pigmentation Function

Regarding the pigmentation function, it was found that sodium acetyl hyaluronate induced a significant increase of HPS4, MITF and ENDR6 genes expressions at transcriptomic level. These results suggest that it could possess a pro-pigmenting property. The effect of sodium acetyl hyaluronate on melanin synthesis in vitro was analysed on melanocyte at basal condition and at stimulated conditions mediated by the addition of L-Tyrosine substrate. Briefly, regarding the basal condition, melanocytes were incubated in 24-wells plate for 24 h of culture. The medium was then replaced by culture medium with or without sodium acetyl hyaluronate or unmodified sodium hyaluronate at concentrations of 0.1, 0.25, 0.5, and 1 mg/ml, respectively, or reference (L-tyrosine 1 mM). Cells were incubated for 10 days with two renewals of the treatment after 3 and 7 days of incubation.

TABLE 6

Impact of sodium acetyl hyaluronate on melanin synthesis in vitro on melanocyte in basal condition (expressed in % of control conditions).

|   |   | Basal |
|---|---|---|
|   | control | 100% |
|   | L-tyrosine 1 mM | 302% (***; +202%) |
| Sodium acetyl hyaluronate | 0.1 mg/ml | 101% (ns, +2%) |
|   | 0.25 mg/ml | 99% (ns; −1%) |
|   | 0.5 mg/ml | 90% (**; −10%) |
|   | 1 mg/ml | 86% (**; −14%) |
| Sodium hyaluronate | 0.1 mg/ml | 103% (ns; +3%) |
|   | 0.25 mg/ml | 90% (***; −10%) |
|   | 0.5 mg/ml | 95% (***; −10%) |
|   | 1 mg/ml | 94% (**; −6%) |

= p < 0.01 ;
*** = p < 0.001;
ns = not significant.
The percentage values in parentheses reflect the effects exerted by the tested compounds (L-tyrosine, sodium acetyl hyaluronate and sodium hyaluronate relative to the performance with no test compound (control)).

The results showed that sodium acetyl hyaluronate induces a decrease of melanin synthesis in basal condition with an effect depending on the dose (+2% at 0.1 mg/ml while −9% at 1 mg/ml). Unmodified sodium hyaluronate was less efficient, demonstrating that acetylation improves the biological activity of sodium hyaluronate.

Stimulation

Regarding the stimulated condition, melanocytes were incubated in 24-wells plates for 24 h of culture. The medium was then replaced by culture medium containing L-tyrosine (1 mM) supplemented by sodium acetyl hyaluronate or unmodified sodium hyaluronate at concentrations of 0.1, 0.25, 0.5, and 1 mg/ml, respectively, or reference (Lipoic Acid 5 μg/ml). Cells were incubated for 10 days with two renewals of the treatment after 3 and 7 days of incubation.

TABLE 7

Impact of Sodium acetyl hyaluronate on melanin synthesis in vitro on melanocyte in stimulated condition (express in % of control L-tyrosine 1 mM condition).

|   |   | Stimulated by l-tyrosine 1 mM |
|---|---|---|
|   | Control (L-tyrosine 1 mM) | 100% |
|   | Lipoic Acid (5 μg/ml) | 27% (***; −73%) |
| Sodium acetyl hyaluronate | 0.1 mg/ml | 105% (**; +5%) |
|   | 0.25 mg/ml | 103% (ns; +3%) |
|   | 0.5 mg/ml | 98% (ns; −2%) |
|   | 1 mg/ml | 89% (***; −11%) |
| Sodium hyaluronate | 0.1 mg/ml | 105% (*; +5%) |
|   | 0.25 mg/ml | 98% (ns; −2%) |
|   | 0.5 mg/ml | 100% (ns) |
|   | 1 mg/ml | 102% (ns; +2%) |

* = p < 0.05;
** = p < 0.01;
*** = p < 0.001;
ns = not significant.
The percentage values in parentheses reflect the effects exerted by the tested compounds (lipoic acid, sodium acetyl hyaluronate and sodium hyaluronate relative to the performance with no test compound (control)).

The results showed that sodium acetyl hyaluronate induces an increase of melanin synthesis with an inverse effect according the doses (+11% at 0.1 mg/ml while −7% at 1 mg/ml). Unmodified sodium hyaluronate was less efficient, demonstrating that acetylation improves the biological activity of sodium hyaluronate.

The invention claimed is:

1. A skin care composition comprising low molecular weight acetylated hyaluronic acid or sodium salt thereof, wherein: the low molecular weight acetylated hyaluronic acid or its sodium salt has a weight average molecular weight of 50 kDa or less and an average degree of O-acetylation of greater than 3.6, wherein the degree of O-acetylation is determined by quantitative 2D NMR.

2. The skin care composition of claim 1, wherein the low molecular weight acetylated hyaluronic acid or its sodium salt has an average degree of O-acetylation of 3.7 or greater.

3. The skin care composition of claim 1, wherein the low molecular weight acetylated hyaluronic acid or its sodium salt has a weight average molecular weight of 35 kDa or less.

4. The skin care composition of claim 1, wherein the low molecular weight acetylated hyaluronic acid or its sodium salt has a polydispersity index that is less than 2.0.

5. A method of preparing low molecular weight acetylated hyaluronic acid or sodium salt thereof having a weight average molecular weight of 50 kDa or less and an average degree of O-acetylation of greater than 3.6, wherein the degree of O-acetylation is determined by quantitative 2D NMR, comprising the steps of: (i) providing a low molecular weight hyaluronic acid having a molecular weight of 50 kDa or less; (ii) subjecting it to acetylation conditions: and, (iii) isolating the low molecular weight acetylated hyaluronic acid.

6. The method of claim 5, comprising the further step of: (iv) reacting the low molecular weight acetylated hyaluronic acid with a base that provides a source of sodium ions to obtain a solution of sodium acetyl hyaluronate.

7. The method of claim 6, wherein the reaction of low molecular weight acetylated hyaluronic acid with a base to obtain the solution of sodium acetyl hyaluronate is carried out at a pH that does not exceed 9.

8. The method of claim 6 comprising the further step of: (v) dehydrating the solution by lyophilization or spray-drying.

9. Low molecular weight acetylated hyaluronic acid or sodium salt thereof having a weight average molecular weight of 50 kDa or less and an average degree of O-acetylation of greater than 3.6, wherein the degree of O-acetylation is determined by quantitative 2D NMR, in the form of a white powder having an L* value of about 90 or more, and a b* value of less than about 8.

10. A method of inhibiting the degradation of the skin's extracellular matrix associated with elevated levels of matrix-degrading enzymes, said method comprising the step of: applying to the skin an effective amount of the skin care composition according to claim 1.

11. The method of claim 10, which causes a reduction in the visible signs of aging on the skin.

12. The method of claim 10, wherein the matrix-degrading enzymes are metalloproteinases.

13. The method of claim 10, wherein the acetylated hyaluronic acid or sodium salt thereof in the skin care composition applied to the skin inhibits the degradation of collagen in the extra-cellular matrix.

14. The skin care composition of claim 2, wherein the average degree of O-acetylation is 3.8 or greater.

15. The skin care composition of claim 3, wherein the average molecular weight is about 30 kDa or less.

16. The skin care composition of claim 4, wherein the polydispersity index is less than 1.8.

17. The method of claim 5, wherein the acetylation conditions comprise: reacting the low molecular weight hyaluronic acid with an acetic acid/acetic anhydride mixture in the presence of a strong acid.

18. A method of inhibiting the degradation of the skin's extracellular matrix associated with elevated levels of matrix-degrading enzymes, said method comprising the step of: applying to the skin an effective amount of the low molecular weight acetylated hyaluronic acid or its sodium salt according to claim 9.

19. The method of claim 12, wherein the metalloproteinases are MMP-1 and/or MMP-3.

* * * * *